United States Patent [19]

Warner

[11] Patent Number: 5,024,095
[45] Date of Patent: Jun. 18, 1991

[54] DIAGNOSTIC LOCATOR FOR MECHANICALLY MALFUNCTIONING ELECTRONIC CIRCUITRY

[76] Inventor: Brian Warner, 36 Austin St., Moonachie, N.J. 07074

[21] Appl. No.: 446,385

[22] Filed: Dec. 5, 1989

[51] Int. Cl.[5] ............................................. G01N 3/34
[52] U.S. Cl. ....................................... 73/661; 73/584; 73/576; 324/537; 324/555
[58] Field of Search ................. 73/572, 574, 576, 579, 73/584, 661, 662, 644; 324/537, 555

[56] References Cited

U.S. PATENT DOCUMENTS

| | | | |
|---|---|---|---|
| 1,970,232 | 8/1934 | Hady | 324/555 |
| 2,020,402 | 11/1935 | Edwards et al. | 324/555 |
| 2,653,297 | 9/1953 | Mohylowski | 324/555 |
| 2,972,069 | 2/1961 | Sproule | 73/644 |
| 3,063,006 | 11/1962 | Steinberger | 324/555 |
| 3,477,280 | 11/1969 | Blackmer | 73/661 |
| 3,919,631 | 11/1975 | Brown | 324/556 |

Primary Examiner—Hezron E. Williams
Assistant Examiner—Rose M. Finley
Attorney, Agent, or Firm—Richard A. Joel

[57] ABSTRACT

A method of diagnosis utilizing a diagnostic locator for detecting sources of electronic circuit malfunction caused by fractured solder connections or other kinetically locatable electronic circuit malfunctions comprises a diagnostic locator using kinetic energy at sonic frequencies which is discriminately applied to particular circuit areas to reveal mechanical intermittance on an accurate basis. The locator includes an elongated nonconductive test probe which is mounted within a housing at one end containing a transducer for kinetically activating the probe. An operator may adjust the kinetic energy being released at the probe tip for greater or lesser propagation upon electronic circuitry being diagnosed. This diagnosis of mechanically malfunctioning electronic circuitry is accomplished while monitoring the output of the circuitry in a conventional manner.

2 Claims, 1 Drawing Sheet

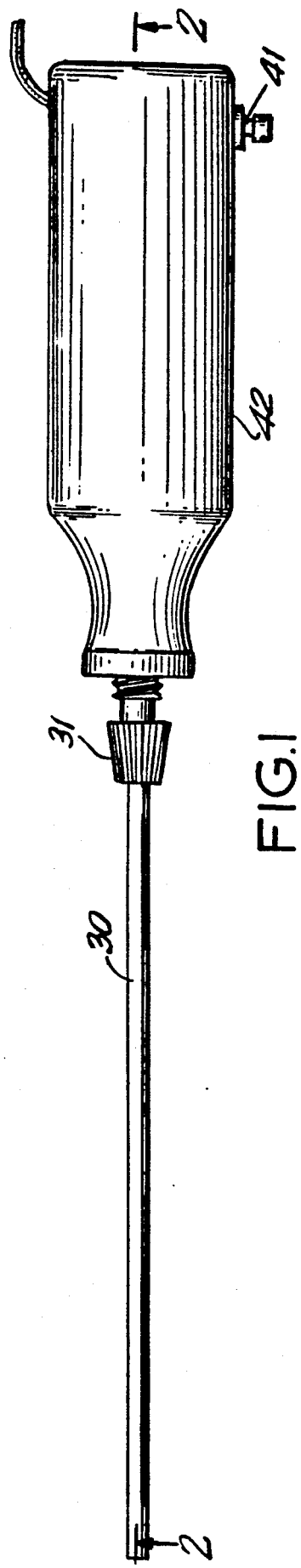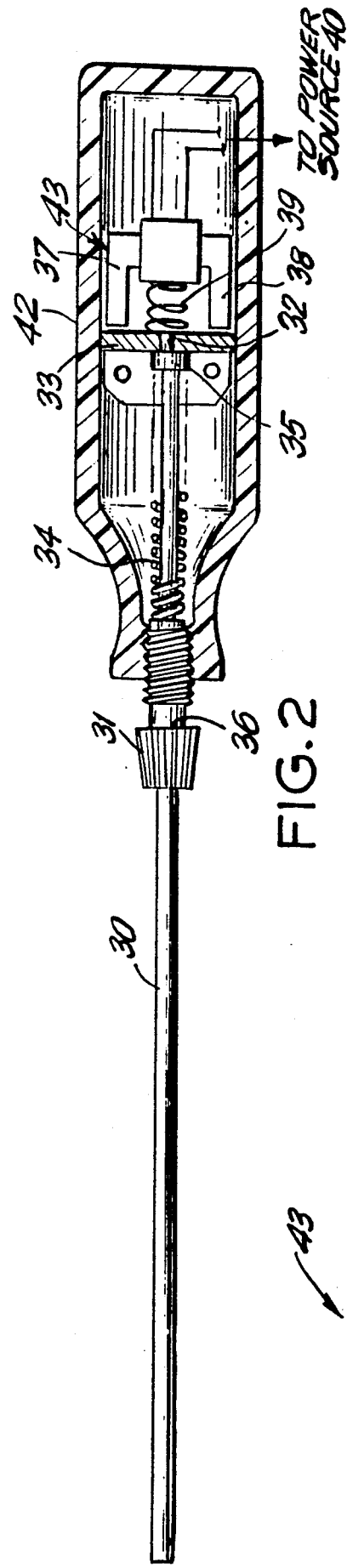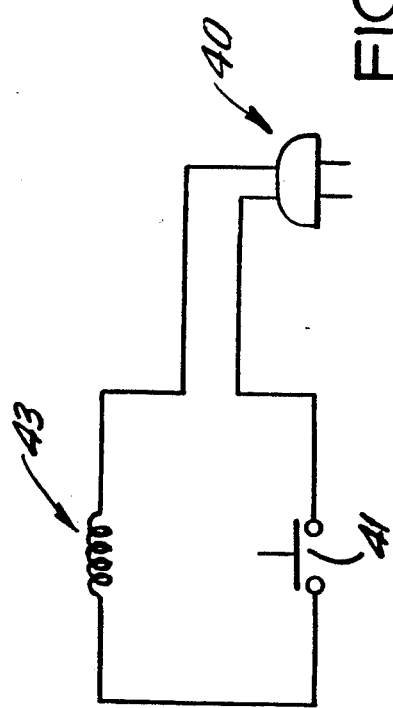

DIAGNOSTIC LOCATOR FOR MECHANICALLY MALFUNCTIONING ELECTRONIC CIRCUITRY

BACKGROUND OF THE INVENTION

In electrical circuits, frequent causes of circuit malfunction are fractured solder connections, open foil etch on circuit boards and mechanical malfunction of components. The normal procedure for locating such malfunctions involves manually tapping around with a non-conductive instrument until the fault is localized. Such a procedure, however, is time consuming, tedious and often undefinitive. Furthermore, the low frequency tapping percussions spread beyond the immediate area, usually making it difficult to accurately pinpoint the cause of malfunction.

The present invention is designed to detect kinetically locatable circuit faults rapidly and with definitive accuracy. The present invention comprises a new diagnostic method utilizing a cost efficient device capable of producing concentrated localized applications of user calibrated kinetic energy at audible sonic frequencies. This energy at high frequencies is then discriminately applied to circuit areas such as printed circuit board or components to kinetically reveal mechanical intermittance. The location of intermittance is picked up by monitoring the circuit in a conventional manner for proper function.

The diagnostic locator of the present invention comprises a non-conductive test probe which is applied to circuitry and uses pinpoint kinetic energy at audible sonic frequencies to determine mechanical intermittance. The prior art, over which the invention is distinguishable, is discussed below.

U.S. Pat. No. 3,919,631 to Brown discloses a self-contained continuity checker having a probe connected to an amplifier which completes a circuit to indicating means. This is in contrast to the mechanical test probe of the present invention which applies energy to the area under test for kinetic test purposes.

U.S. Pat. No. 2,653,297 to Mohylowski discloses a testing device having a spring-backed probe which generates a spark as an indicator that a circuit break exists. Also of interest are U.S. Pat. Nos. 2,020,402, 1,970,232 and 3,063,006. None of the foregoing patents disclose the use of a sonically vibrating probe to locate circuit faults.

SUMMARY OF THE INVENTION

The present invention comprises a test probe having an electrically non-conductive tip at one end and which is mounted within a housing at the other end. The invention also comprises a new and improved method for diagnosing kinetically locatable electronic circuit malfunctions of a mechanicallly intermittent nature. The probe, typically of flexible non-conductive fiber glass, is mounted within a housing at one end while the other end is used to contact the circuit.

Electro-magnetic means cause the tip to vibrate. As the frequency of vibration is lowered, the propagation of probe transmitted kinetic energy increases due to lower acoustical impedance presented by the electronic circuitry being tested. As amplitude of test probe kinetic energy is increased the propagation of transmitted energy upon circuitry increases. The circuit performance is monitored by conventional means so that the fault is relevant when the probe transmitted energy encounters the trouble area.

Accordingly, it is an object of this invention to provide a new and improved method for circuit diagnosis by accurately applying kinetic energy at audible sonic frequencies to determine circuit faults.

Another object of this invention is to to provide a new and improved expedient method for accurately detecting kinetically locatable electronic circuit faults.

A further object of this invention is to provide a new and improved testing device for circuit malfunctions of a mechanical nature which is simple, inexpensive, and easy to use.

A more specific object of this invention is to provide a new and improved testing method and device for locating mechanical circuit faults by applying predetermined user adjustable kinetic energy at audible sonic frequencies to specific circuit locations with a non-conductive test probe while monitoring the circuitry being tested for performance to verify and localize precise point of mechanical intermittence.

BRIEF DESCRIPTION OF THE DRAWINGS

The above and other objects and advantages of the present invention may be more clearly realized when viewed in conjunction with the accompanying drawings wherein:

FIG. 1 is a side view of the testing device comprising the present invention;

FIG. 2 is a cross-sectional view of the invention taken along the line 2—2 of FIG. 1;

FIG. 3 is a schematic circuit diagram for the alternating current powered version of the invention.

DETAILED DESCRIPTION OF THE INVENTION

The present invention as shown in the drawings, comprising a new, more accurate and expedient method for diagnosing kinetically locatable electronic circuit malfunctions of a mechanical nature and the associated device consisting of a rod shaped test probe 30 made of any characteristic non-conductive material with similar tensive qualities and the strength of fiberglass. The rod shaped probe 30 can flex to reach difficult circuit locations and extends through an adjustable bushing/ coupling 31 into the housing 42 where it is mounted upon a transverse metal bar 33 at its other end. The internally mounted portion of the test probe includes a coiled spring 34 wrapped thereabout which retains the rod 30 mounted upon the metal bar 33 which is held in equilibrium by an opposing, suitably gauged return spring 39. The metal bar 33 vibrates due to the alternating magnetic field generated by a U-shaped electromagnet 43, forming a transducer which imparts the vibratory energy to the test probe 30. The adjustable bushing 31 presets tension upon the coiled spring 34 providing user calibration of test probe kinetic force for the desired propagation of probe transmitted kinetic energy.

Frequency of probe operation is dependent on transducer response and is operated in the audibly sonic range by user choice of the frequency of alternating electric current used to energize the electromagnet and thus excite the transducer. As frequency is lowered, propagation of probe transmitted kinetic energy increases due to lower acoustical impedance presented by printed circuit boards and components at lower frequencies. As frequency is increased, propagation of vibratory energy becomes very localized. The above mentioned force adjustment will provide substantial user control over propagation of probe transmitted kinetic energy in the audibly sonic range. A switch 41 activates the above mentioned transducer upon user discretion by energizing the electromagnet with a alternating current power source.

In greater detail, the probe 30 comprises an elongated non-conductive plastic member of a material such as fiberglass. The probe 30 extends through an aperture in the enlarged tapered knurled threaded coupling 31 having a rear threaded portion of lesser diameter and engages a recess 32 in the metal block 33. The probe 30 is maintained in position by spring 34 which engages the projecting portion 35 at one end and the rear portion 36 of the coupling 31 at its other end. The metal block 33 is suspended above the laminated electromagnet members 37 and 38 by return spring 39. The electromagnet 43 is connected to a power source 40 through a switch 41. The frequency of probe operation is determined per frequency of alternating current power source 40. Activation of the electromagnet 43 by switch 41 which extends through the housing 42 causes vibration of the metal block 33 which engages the probe 30 to cause movement thereof. The probe 30 then vibrates at twice the frequency of alternating current energy being applied to electromagnet 43.

In operation, the test probe 30 detects kinetically locatable mechanically intermittent malfunctions by the following method. To determine the presence of mechanically intermittent malfunctions the fiberglass probe 30 which is flexible to reach inaccessible circuit areas, is adjusted for greater amplitude of kinetic force and applied to various suspect areas to localize the source of malfunction.

The threaded coupling 31 may be rotated to increase or decrease the amplitude of probe transmitted kinetic force to troubleshoot larger or smaller areas on Printed Circuit board or other circuitry. More kinetic force will test larger areas. With reduced kinetic force applied by the probe 30, one can pinpoint the specific source of malfunction. One can also troubleshoot from the component side of Printed Circuit board to buzz and locate individual suspected components which may show mechanical intermittence. The invention greatly reduces diagnostic time and increases the accuracy of the fault finding process.

The new method for proficient localization of kinetically locatable mechanically intermittent electronic circuit malfunction utilizes precise probe applied audible sonic frequency kinetic energy between fifty-nine (59) cycles per second and 16,000 cycles per second. As frequency is lowered, propagation of probe transmitted kinetic energy increases upon the circuitry. As amplitude of probe transmitted kinetic energy is increased, propagation upon circuitry increases. To utilize the Diagnostic Locator, first the operator checks means to monitor the performance of circuitry being tested such as the audio/visual indications of a television itself or an oscilloscope or other convenient conventional means to monitor performance of circuitry being tested for mechanical intermittence. Then the Diagnostic Locator is adjusted for increased propagation and the test probe is placed in contact and activated upon generalized areas of circuitry being tested. When approaching the location of mechanically intermittent malfunction in circuit, the circuit performance being monitored in conventional manner will indicate general location of malfunction by fluctuating to normal operation for circuit.

Once the general location of mechanical intermittence is determined, the Diagnostic Locator is adjusted for reduced propagation of test probe transmitted kinetic energy to further localize the area with the source of malfunction. After repeated diagnostic localization with further reductions of propagation regarding probe transmitted kinetic energy, the specific source of mechanical intermittence within circuitry under diagnosis can be determined.

Although there may be minor variations of procedure determined by individual application or use, the steps outlined above are the basis diagnossic procedure utilizing the new method.

It is understood that the above-described arrangements are merely illustrative examples of the application. Numerous other arrangements may be readily devised by those skilled in the art which will embody the principles of the invention and fall within the spirit and scope thereof.

What is claimed is:

1. A method for detecting kinetically locatable mechanically intermittent sources of electronic circuit malfunction with a diagnostic locator comprises the steps of:

applying a vibratory test probe form the locator to the electronic circuit, monitoring performance of circuitry being tested to detect presence of mechanical intermittence when probe energy is applied, adjusting the diagnostic locator for increased propagation of test probe transmitted kinetic energy, activating the test probe upon generalized areas of circuitry to determine the presence of mechanically intermittent electronic circuit malfunction, adjusting the diagnostic locator for reduced propagation of probe transmitted kinetic energy, in response to detecting the presence of a mechanically intermittent circuit malfunction, and applying probe transmitted energy to the area of circuitry where presence of malfunction was detected to further localize specific source of mechanically intermittent electronic circuit malfunction, and performing repeated diagnostic localization for further reductions of propagation with the test probe transmitted kinetic energy to determine the specific source of the kinetically locatable mechanically intermittent electronic circuit malfunction.

2. A diagnostic locator for detecting kinetically locatable mechanically intermittent sources of electronic circuit malfunction comprises:

a non-conductive test probe comprising an elongated flexible fiberglass rod, a housing, means coupling the probe within the housing at one end comprising an enlarged tapered portion having a knurled surface at one end and a rear threaded portion of lesser diameter and an axial aperture in the housing through which the probe extends, wherein the coupling means can be adjusting to vary the amplitude of the vibrating probe transmitted energy, resilient means mounted about the probe within the housing to apply a predetermined pressure on the probe, electromagnetic means coupled to the probe within the housing to cause vibration of the probe and a power source for activating said means, the electromagnetic means comprising a transducer mounted within the housing including a metal block having a recess within which one end of the test probe is seated and a U-shaped electromagnet means engaging the metal block to cause vibration of the test probe, a switch connecting the power source to the electromagnetic means and extending through the housing for ease of actuation, and wherein the vibrating probe is placed in contact with electronic circuit areas and actuated to determine sources of mechanically intermittent circuit malfunctions.

* * * * *